(12) United States Patent
Fukuoka et al.

(10) Patent No.: US 10,682,456 B2
(45) Date of Patent: *Jun. 16, 2020

(54) PACKAGE FOR INFUSION SET

(71) Applicant: KOBAYASHI & CO., LTD., Tokyo (JP)

(72) Inventors: Koji Fukuoka, Kobe (JP); Go Kawaoi, Kobe (JP); Kazuyuki Osawa, Kobe (JP); Imari Endo, Kobe (JP)

(73) Assignee: KOBAYASHI & CO., LTD., Tokyo (JP)

( * ) Notice: Subject to any disclaimer, the term of this patent is extended or adjusted under 35 U.S.C. 154(b) by 125 days.

This patent is subject to a terminal disclaimer.

(21) Appl. No.: 15/549,530

(22) PCT Filed: Feb. 10, 2015

(86) PCT No.: PCT/JP2015/053571
§ 371 (c)(1),
(2) Date: Aug. 8, 2017

(87) PCT Pub. No.: WO2016/129048
PCT Pub. Date: Aug. 18, 2016

(65) Prior Publication Data
US 2018/0021504 A1    Jan. 25, 2018

(51) Int. Cl.
*A61M 5/00*     (2006.01)
*A61J 1/14*     (2006.01)
(Continued)

(52) U.S. Cl.
CPC ............... *A61M 5/002* (2013.01); *A61J 1/14* (2013.01); *A61M 5/14* (2013.01); *A61M 5/1409* (2013.01); *A61M 5/158* (2013.01); *B65D 2203/00* (2013.01)

(58) Field of Classification Search
CPC ..... A61B 19/02; A61J 1/14; A61J 1/20; A61J 1/2093; A61M 5/00; A61M 5/002;
(Continued)

(56) References Cited

U.S. PATENT DOCUMENTS 3,858,717 A * 1/1975 Peters .................. B65D 5/4216
206/459.5
4,195,059 A * 3/1980 Whitcher .................. B01L 9/54
206/459.5
(Continued)

FOREIGN PATENT DOCUMENTS

JP       3-41454 U1     4/1991
JP       6-105890 A     4/1994
(Continued)

OTHER PUBLICATIONS

International Search Report dated Apr. 7, 2015, issued in counterpart International Application No. PCT/JP2015/053571 (2 pages).

*Primary Examiner* — Byron P Gehman
(74) *Attorney, Agent, or Firm* — Westerman, Hattori, Daniels & Adrian, LLP

(57) ABSTRACT

In the context of a package for sealing an infusion set therewithin, the present invention causes a plurality of illustrations in which elements and colors thereof which appear in a story, verse, or lyric of a song or nursery rhyme are depicted in images in order of appearance therein, the respective images being displayed on a surface of the package in order from frontmost to backmost in mutually offset and partially overlapping fashion, such that it is possible to extremely naturally and without difficulty grasp the colors and the order thereof, i.e., the order of administration, as a result of which it is possible to effectively prevent misidentification of administration procedure during use of the infusion set. Furthermore, by further causing numbers indicating order of administration to be displayed
(Continued)

at the respective colored illustrations, the order of use of the respective sets of infusions in the infusion set can be linked to colors and definitively recognized, making it possible to greatly reduce the likelihood of occurrence of human error.

2 Claims, 3 Drawing Sheets

(51) Int. Cl.
*A61M 5/14* (2006.01)
*A61M 5/158* (2006.01)

(58) Field of Classification Search
CPC ...... A61M 5/14; A61M 5/1409; A61M 5/158; A61M 5/162; A61M 25/00; A61M 25/02; A61M 25/16; B65D 2203/00; B65D 85/00
USPC .................................. 206/363–370, 459.5
See application file for complete search history.

(56) References Cited

U.S. PATENT DOCUMENTS

| | | | | |
|---|---|---|---|---|
| 5,182,895 A * | 2/1993 | Lugo | ............... | A45C 3/04 206/459.5 |
| 5,888,408 A * | 3/1999 | Nagels | ............... | A61J 1/10 604/408 |
| 8,597,271 B2 * | 12/2013 | Langan | ............... | A61M 5/1417 604/189 |
| 8,844,556 B2 * | 9/2014 | Honma | ............... | A61M 5/36 137/197 |
| 2004/0097896 A1 | 5/2004 | Raufman et al. | | |
| 2005/0011793 A1 * | 1/2005 | Sapyta | ............... | A45C 7/0095 206/459.5 |
| 2007/0199848 A1 * | 8/2007 | Ellswood | ............... | A61B 42/40 206/459.5 |
| 2012/0150123 A1 * | 6/2012 | Lawrence | ............... | A61M 5/158 604/180 |
| 2013/0274702 A1 * | 10/2013 | Miyasaka | ............... | A61M 39/20 604/403 |
| 2016/0000652 A1 * | 1/2016 | Rose | ............... | A61J 1/10 604/244 |

FOREIGN PATENT DOCUMENTS

| | | |
|---|---|---|
| JP | 8-336601 A | 12/1996 |
| JP | 2003-509163 A | 3/2003 |
| JP | 2003-265622 A | 9/2003 |
| JP | 2004-217769 A | 8/2004 |
| JP | 2004-267377 A | 9/2004 |
| JP | 2010-18539 A | 1/2010 |
| JP | 2014-217555 A | 11/2014 |
| JP | 5774258 B1 | 9/2015 |

* cited by examiner

PACKAGE FOR INFUSION SET

TECHNICAL FIELD

The present invention relates to a package for an infusion set that does not cause occurrence of misidentification of administration procedure.

BACKGROUND ART

Medical treatments have conventionally been carried out in which therapeutic medications are formulated as infusions which are administered intravenously. Infusions employing therapeutic medications in the form of anticancer agents, nutrients, and the like must typically be administered in high dosages. Furthermore, where a plurality of medications are combined, each infusion must be administered in order, and the total administration dosage is quite high. On the other hand, as administration of infusions continues, because a sudden rise in the concentration of a drug within the blood increases the risk of occurrence of anaphylactic shock, cardiac arrhythmia, and other such side effects, there is a need for physicians and nurses to carefully continue to adjust infusion administration dose while monitoring the condition of the patient. However, carrying out administration by adjusting amount by means of injection is difficult, and as administration time goes on and the number of administrations increases, the patient experiences an increasing amount of bodily pain and is placed under an increasing amount of stress. For this reason, intravenous drip infusion is widely used as a technique for easily and continuously administering infusions to patients intravenously. During intravenous drip infusion, an infusion set is employed as medical equipment for causing a container having an infusion sealed therewithin to be connected to an intravenous drip needle that has been inserted within a blood vessel of the patient.

Infusion sets in general use conventionally employ soft tubing to link the container having the infusion sealed therewithin with the intravenous drip needle, a mechanism employing a roller clamp and a drip chamber being provided midway along said soft tubing. In addition, infusion sets have moreover been proposed in which the arrangement is split into multiple sets of infusions to link a plurality of containers having infusions sealed therewithin for the purpose of accommodating medical treatment in which a plurality of infusions are continuously administered in sequence (see Patent Reference No. 1 and Patent Reference No. 2).

Furthermore, where a plurality of medications were administered in the form of infusions, particular attention has been required so as to avoid mixture of solutions for which mixture is contraindicated and so as to see that administration is carried out in the correct order. Because the type and number of therapeutic agents are different for every patient, infusion sets must be prepared that are reassembled in correspondence thereto. However, it is often the case that the containers employed for infusions have similar external appearance. For this reason, mixups with respect to the order in which spikes pierce containers, confusion as to which infusion line should be used for different anticancer agent solutions, mistaken order of administration, and other such accidents can easily occur.

Measures have therefore been adopted by applying labels to the various containers at the time that the infusions are prepared, attaching written warnings, and so forth to clearly specify administration procedure, and to make the various containers recognizable. Furthermore, measures have been adopted in attempts to prevent mistaken attachment of medical equipment through employment of colored molded members made of plastic and so forth (see Patent Reference No. 3).

However, there has been a need for an infusion set to be provided at a site where medical treatment is carried out in such fashion as to permit it to be ready for instant use. There has therefore been provision of a manufactured infusion set which is sterilized in advance, this then being sealed within a sterilized pouch-like package (see Patent Reference No. 4).

PRIOR ART REFERENCES

Patent References

Patent Reference No. 1: Japanese Patent Application Publication Kokai No. H08[1996]-336601
Patent Reference No. 2: Japanese Patent Application Publication Kokai No. 2003-265622
Patent Reference No. 3: Japanese Patent Application Publication Kokai No. 2004-217769
Patent Reference No. 4: Japanese Patent Application Publication Kokai No. 2014-217555

SUMMARY OF INVENTION

Problem to be Solved by Invention

A problem to be solved by the present invention is to provide a novel package for providing an infusion set sealed therewithin that preemptively prevents occurrence of accidents in which there is confusion about which infusion is which among multiple pieces of infusion tubing and/or error in the order in which infusions are to be administered such as may occur as a result of misidentification of the procedure for use of an infusion set that is provided with a plurality of spikes, and for which it is easy to establish standard procedures for use.

Means for Solving Problem

A first means in accordance with the present invention for solving the foregoing problems is a package for sealing an infusion set therewithin characterized in that displayed in mutually offset and partially overlapping fashion on a surface thereof are a plurality of illustrations that are displayed with respectively different colors.

A second means in accordance with the present invention for solving the foregoing problems is the package for sealing the infusion set therewithin according to the first means in accordance with the present invention characterized in that the aforesaid plurality of illustrations employ elements and colors thereof which appear in a story, verse, or lyric of a song or nursery rhyme, these being depicted in images in order of appearance therein, the respective images being displayed in order from frontmost to backmost in mutually offset and partially overlapping fashion.

A third means in accordance with the present invention for solving the foregoing problems is the package for sealing the infusion set therewithin according to the first or second means in accordance with the present invention characterized in that the aforesaid infusion set is such that a spike cap; a spike on which said spike cap is installed; infusion tubing, one end of which is connected to said spike; a shutoff clamp for pressing on said infusion tubing and opening and/or closing a flow path within said infusion tubing; and a stopcock and/or splitter which is connected to the other end of said infusion tubing are grouped together as a single group, respective groups being given different colors, colors being assigned so as to indicate an order in which spikes are to be used during intravenous drip infusion, one or more of the constituent elements of each group being colored with the color assigned for that group, the order of those colors being identical to the order of colors employed at the images displayed on the aforesaid package.

A fourth means in accordance with the present invention for solving the foregoing problems is the package for sealing the infusion set therewithin according to any one of the first through third means in accordance with the present invention characterized in that numbers indicating order of administration are further displayed at the aforesaid illustrations.

BENEFIT OF THE INVENTION

A package for sealing an infusion set therewithin in accordance with the present invention is such that displayed in mutually offset and partially overlapping fashion on a surface thereof are a plurality of illustrations that are displayed with respectively different colors, the order of those colors corresponding to an order of colors assigned to respective groups in correspondence to an order of use of spikes at the infusion set which is sealed within said package. This makes it possible to obtain the benefit whereby an order of colors is associated with an order of administration of infusions and/or a procedure for using the infusion set, making it possible to facilitate identification of sets of secondary tubing of different groups.

Moreover, at the infusion set of the present invention, by causing the aforesaid colors and the order thereof to be adopted from those in a familiar verse or lyric of a nursery rhyme, and by moreover causing illustration(s) in which colored images associated with the aforesaid verse or lyric of a nursery rhyme based on which these were adopted to be displayed in layered fashion on a package within which the infusion set is sealed, it will be possible to naturally and accurately recognize the order of colors, i.e., the procedure for use of the infusion set and/or the order of administration of infusions, making easy memorization in association with such familiar content possible, and making it possible to more effectively prevent misidentification of administration procedures. In addition, when this is viewed by patients, nurses, and physicians, it will alleviate tension, and will make it possible to simultaneously obtain a psychological effect whereby the atmosphere at sites at which medical treatment is carried out is made more relaxing.

In addition, provision of the infusion set of the present invention will permit smooth progress to be made in standardization of operational procedures for use of the infusion set, and will make it possible to obtain the benefit whereby medical accidents such as mistaken administration or the like occurring as a result of misidentification by a pharmacist, physician, or nurse, or other such human error, are prevented.

EMBODIMENTS FOR CARRYING OUT THE INVENTION

Below, embodiments for carrying out the present invention are described as appropriate with reference to the drawings.
Configuration and Constitution of Package for Sealing Infusion Set Therewithin, and of Infusion Set Sealed Therewithin, in Accordance with Present Invention So long as it is of a form such as will allow the sterilized infusion set to be sealed therewithin and to be provided in such fashion as to permit it to be ready for instant use, anything meeting may be used as the package for sealing the infusion set therewithin in accordance with the present invention. Based upon considerations of manufacturing cost, it is preferred that a pouch-like package be employed.

Figure 2:
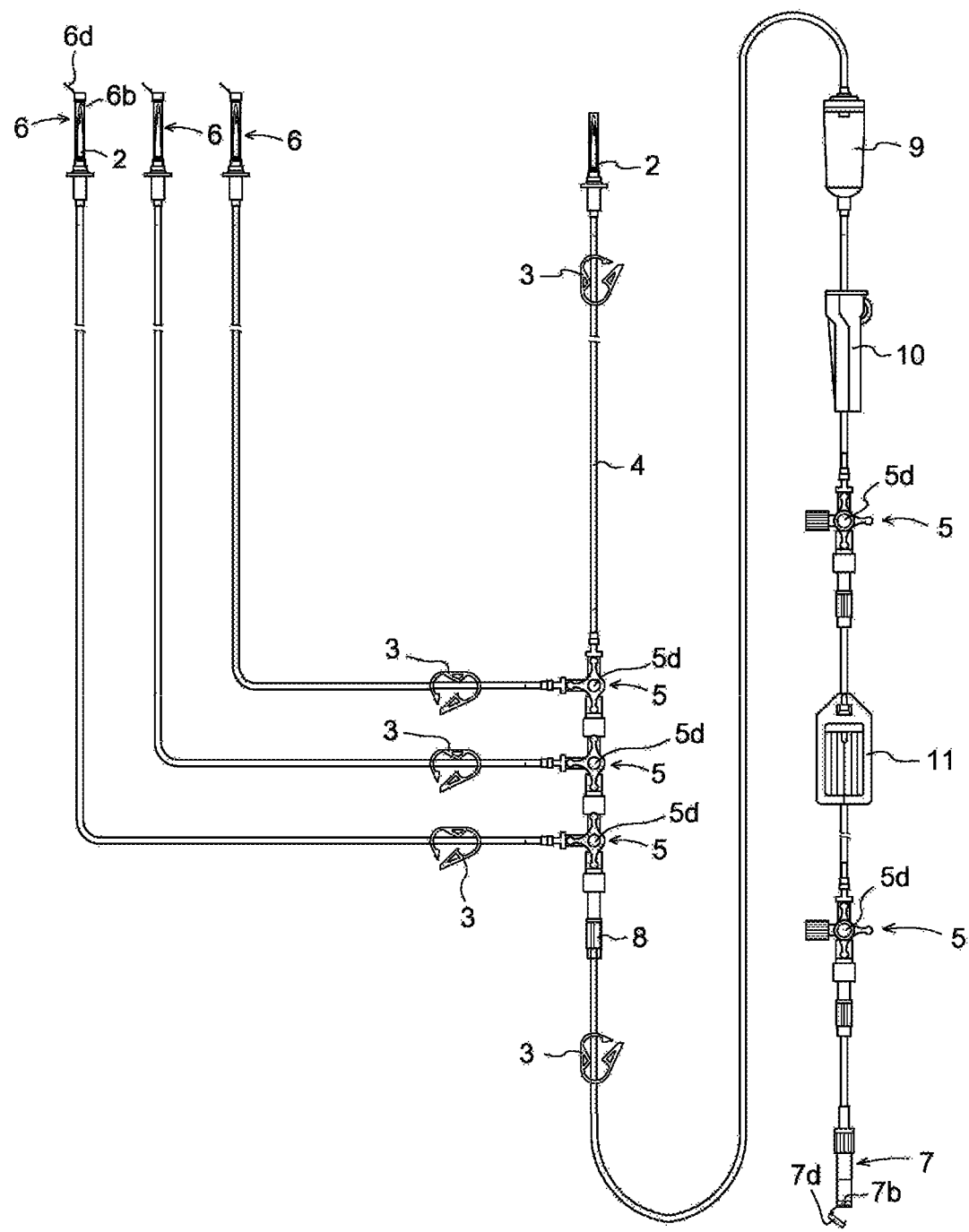
FIG. 2 Explanatory diagram showing an example of an infusion set that may be sealed within a package for sealing an infusion set therewithin in accordance with the present invention. Shown is an infusion set having spikes and tubing linked to three different sets of secondary tubing corresponding to the three colors, i.e., red, white, and yellow, at the tulips.
Figure 3:
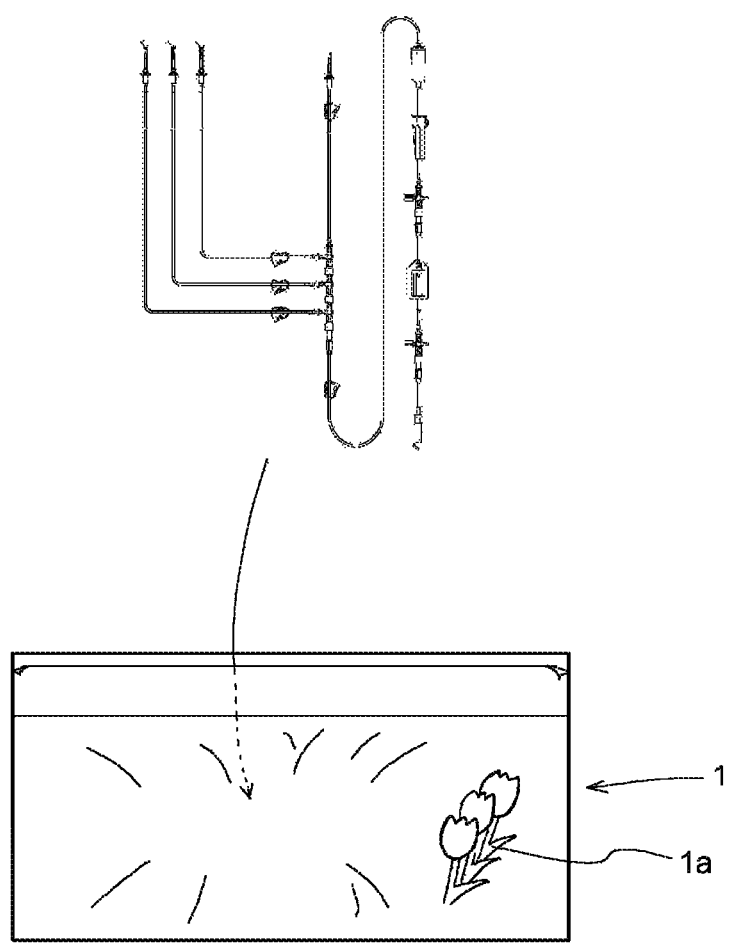
FIG. 3 Drawing for explaining how a corresponding infusion set may be sealed within a package for sealing an infusion set therewithin in accordance with the present invention.

An infusion set to be sealed within a package in accordance with the present invention has members in the form of spike cap(s) 2, 6; spike(s) 2; infusion tubing 4; shutoff clamp(s) 3 for pressing on and opening and/or closing flow path(s) within infusion tubing; three-way stopcock(s) 5 and/or other such stopcock(s) and/or splitter(s); male connector(s); drip chamber(s) 9; roller clamp(s) 10; connector(s) for connection with intravenous drip needle(s); cap(s) for connector(s) for connection with intravenous drip needle(s); and optional filter bag(s) 11, there being a plurality of sets of secondary tubing by virtue of three-way stopcock(s) 5 and/or other such stopcock(s) and/or splitter(s) (FIG. 2).

An infusion set employed so that it might be sealed within the package of the present invention may be such that three-way stopcock(s) 5 and/or other such stopcock(s) and/or splitter(s) at which infusion tubing 4 is connected to secondary tubing branch connector(s) 5c, said infusion tubing 4, shutoff clamp(s) 3 linked thereto, spike(s) 2, and spike cap(s) 6 may be grouped together as a single group such that one or more thereamong is colored with the same color. Moreover, where said infusion set has a plurality of three-way stopcocks 5 and/or other such stopcocks and/or splitters at which spikes 2 are connected to secondary tubing, groups belonging to adjacent three-way stopcocks 5 and/or other such stopcocks and/or splitters may be colored so as to be respectively different colors. Where coloring is carried out, respective groups are colored so as to be of different colors in correspondence to the order in which infusion(s) is/are to be administered so as to permit identification thereof.

However, despite attempts to memorize whatever unremarkable order of colors may have been established, where there is no deep meaning attached to the colors and/or order thereof, there is a risk that the colors and/or order thereof will be misidentified, for which reason particularly careful attention is demanded of nurses and physicians.

To avoid risk of misidentification, it is preferred that colors and an order thereof such as appear in a nursery rhyme, lyric, or verse that many people will know, having been familiar therewith from a young age, be employed as the colors and order thereof for identifying the aforesaid respective groups. For example, where provided in Japan, the colors and order indicated by "red, white, yellow" appearing in lyrics about tulips in the nursery rhyme might be employed; or where provided in an English-speaking region, the colors and order indicated by "red, blue, white" in the verse which goes roses are red, violets are blue, sugar is sweet, and so are you that comes from Mother Goose might be employed, respective groups being colored with different colors in order of use so as to permit identification thereof.

By thus causing an infusion set to employ coloration constituted so as to permit colors and order thereof to be memorized in association with lyrics, verses, and/or other such familiar content, as compared with memorization of an unremarkable order of colors established in the context of standardized administration procedures, nurses and physicians can more naturally and accurately recognize order of colors, i.e., procedures for use of the infusion set and/or order of administration of infusions, and as easy memorization in association with such familiar content is facilitated, it is possible to more effectively prevent misidentification of administration procedures. Moreover, this will permit smooth progress to be made in standardization of operational procedures for preventing misidentification of administration procedures at sites where many nurses and physicians are engaged in medical treatment.

In addition to the aforesaid coloration, it is possible by further optionally causing number(s) indicating order(s) of administration to be displayed at any among three-way stopcock(s), infusion tubing, shutoff clamp(s), spike(s), cap(s) for installation on spike(s), and/or colored tape(s), to even more effectively prevent misidentification of standardized administration procedures.

An infusion set provided with coloration and optionally with display of numbers indicating order of administration as described above is sealed within a pouch or other such package 15 and is provided to a site at which medical treatment is carried out. Here, to even further increase the effect whereby misidentification of standardized administration procedures may be prevented as a result of coloration and display of number(s) indicating order(s) of administration, the infusion set may be sealed within a package at which displayed in mutually offset and partially overlapping fashion on the surface thereof are a plurality of illustrations ((a) at FIG. 1). It is preferred that the infusion set be such that the foregoing illustrations are respectively colored so as to have the same colors as the coloration given to groups within the infusion set comprising the aforesaid three-way stopcocks at which infusion tubing is connected to secondary tubing branch connectors, said infusion tubing, shutoff clamps linked thereto, spikes, and caps for installation on spikes, and so as be colored in order from the frontmost illustration to the backmost illustration in correspondence to the order of use ((b) at FIG. 1). It is more preferred that the aforesaid colored illustrations be such that numbers indicating order of administration be displayed thereon in ascending order from the frontmost illustration to the backmost illustration ((c) at FIG. 1).

From frontmost to backmost, the illustrations on the aforesaid package should respectively employ, and be respectively colored, in order of appearance of images associated with a familiar story, verse, or lyric of a nursery rhyme based on which coloration of the infusion set is carried out. By thus providing an infusion set sealed within a package displaying illustrations, nurses and physicians can, merely by looking at the package before or after the package is opened, extremely naturally and without difficulty grasp the colors and the order thereof, i.e., the order of administration, memorized in association with lyrics, verses, and/or other such familiar content, making it possible to more effectively prevent misidentification of standardized administration procedures. Moreover, by causing numbers indicating order of administration to be displayed at the respective colored illustrations, the order of use of the respective sets of infusions in the infusion set can be linked to colors and definitively recognized, making it possible to greatly reduce the likelihood of occurrence of human error.

Moreover, an infusion set sealed within a package displaying illustrations such as images associated with the aforesaid familiar verse or lyric of a nursery rhyme, when viewed by patients, nurses, and physicians will also alleviate tension, making it possible to simultaneously obtain a psychological effect whereby the atmosphere at sites at which medical treatment is carried out is made more relaxing.

Materials

There is no particular limitation with regard to the materials that may be employed for formation of the members that make up the infusion set of the present invention, it being possible to use materials such as are ordinarily employed in the context of members for infusion sets and medical equipment; for example, Nylon, polycarbonate, polypropylene, polystyrene, and/or other such resin materials and/or stainless steel and/or other such metals may be employed, it being possible to employ polyolefinic resins and/or other such materials suitable for soft tubing at the infusion tubing. Because, depending on the type of drug, e.g., anticancer agent, used, polyethylene terephthalate (PEHP) serving as plasticizer may leach from polyvinyl chloride (PVC), resin materials employed for formation of the members that make up the infusion set of the present invention do not employ polyvinyl chloride, it being preferred that these employ Nylon and/or polycarbonate. Hydrophobic filter(s) may employ polytetrafluoroethylene (PTFE), polyethylene (PE), polyolefin, polypropylene, polyethylene, polyvinylidene fluoride (PVDF), nitrocellulose, and/or the like, it being preferred that polyethylene (PE) and/or polytetrafluoroethylene (PTFE) be employed therefor. Any of the various foregoing resin materials may be employed in colored form. Furthermore, stainless steel and/or other metals may be employed in a form in which the surface thereof has undergone coloration treatment, in which case it is preferred that material(s) which have undergone coloration treatment that is highly anticorrosive be employed.

Manufacturing Operations

The infusion set of the present invention is manufactured in such fashion that the respective members are definitively connected so as to form an infusion set in the form of a single integral unit. There is no particular limitation with regard to the method for definitively connecting the respective members, it being possible to use methods such as are ordinarily employed as methods for obtaining an infusion set or medical equipment in the form of a single integral unit; for example, adhesive operations employing adhesives ordinarily used for infusion sets or other such medical equipment, fusing operations that make use of heat, ultrasonic waves, or the like, and/or other such techniques may be utilized. By providing the infusion set in the form of a single integral unit, the risk that joined parts will become separated is eliminated, making it possible to more definitively prevent medical accidents such as damage to equipment and/or contamination of the hospital room interior due to occurrence of unintentional leakage of liquid.

Moreover, so as to permit immediate commencement of priming and backpriming operations after the package has been opened and the infusion set has been removed therefrom, an infusion set in accordance with the present invention may be provided in presterilized form. There is no particular limitation with regard to the method for sterilization of the infusion set, it being possible to use methods such as are ordinarily employed as methods for sterilization of infusion sets and/or medical equipment; for example, methods which include ethylene oxide gas sterilization, γ irradiation sterilization, e-beam sterilization, radiation sterilization, ultraviolet irradiation sterilization, hydrogen peroxide sterilization, and ethanol sterilization may be employed. In addition, as said sterilization method, it is preferred based on considerations which include ease of manufacturing and cost reduction that ethylene oxide gas sterilization, e-beam sterilization, and/or γ irradiation sterilization be employed. It is preferred that e-beam sterilization be carried out to such a degree as will not cause degradation of the infusion set, and it is preferred that the irradiative energy during γ irradiation sterilization be within a range that is up to on the order of 5 kGy to 30 kGy so as to cause sterilization to be carried out to such a degree as will not cause degradation of the infusion set.

WORKING EXAMPLES

Indicated below are working examples of manufacture and use of infusion sets in accordance with the present invention. The present invention is not to be limited in any way by these descriptions.

Members for constructing an infusion set in accordance with the present invention were prepared in the form of a cap, for installation on a spike, arranged at which there was an opening configured so as to not allow passage therethrough of solid or liquid but so as to allow passage therethrough of gas at the interior of the cap, a hydrophobic filter being arranged at a location inward from where the tip of the spike was inserted at the interior of the cap by way of an insertion port for the spike, and a lid at the exterior of said opening for closing said opening; a spike; a three-way stopcock having a primary tubing downstream branch connector equipped with a mechanism that connected in such a fashion as to permit rotation about primary tubing as axis; a male connector; a drip chamber; a roller clamp; a connector for connection with an intravenous drip needle; infusion tubing; a shutoff clamp for pressing on and opening and/or closing flow path(s) within infusion tubing; an optional filter bag; and a cap, for installation on a connector for connection with an intravenous drip needle, arranged at which there was an opening configured so as to not allow passage therethrough of solid or liquid but so as to allow passage therethrough of gas at the interior of the cap, a hydrophobic filter being arranged at a location inward from where the tip of the connector for connection with the intravenous drip needle was inserted at the interior of the cap by way of an insertion port for the connector for connection with the intravenous drip needle, and a lid at the exterior of said opening for closing said opening.

The foregoing members were connected to form of a single integral unit as described at the section entitled Configuration and Constitution of Infusion Set of Present Invention and the section entitled Manufacturing Operations. In addition, caps for installation on spikes provided with lids and caps for installation on connectors for connection with intravenous drip needles provided with lids were definitively installed thereon, lids of the respective caps were opened, all shutoff clamps were placed in their open states, levers of three-way stopcocks at which infusion tubing connected to spikes were connected at secondary tubing branches were moved to positions permitting flow to/from all three branches, levers of three-way stopcocks for use as emergency ports at which there were no spikes or infusion tubing connected at secondary tubing branches were moved to positions permitting flow to/from primary tubing upstream branches and primary tubing downstream branches but not permitting flow to/from secondary tubing branches, and roller clamp 3 was placed in its open state, to manufacture an infusion set in accordance with the present invention.

Figure 1:
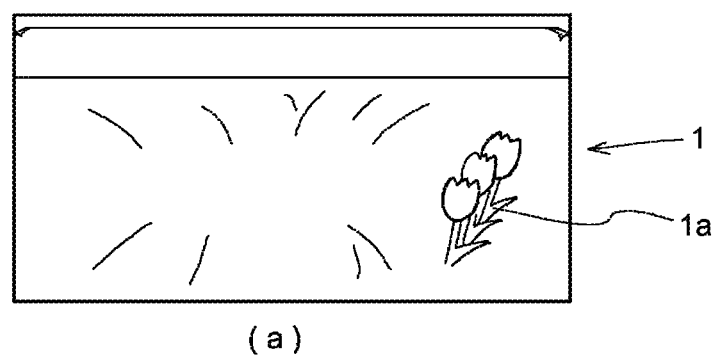
FIG. 1 Explanatory diagram showing a package for sealing an infusion set therewithin in accordance with the present invention. (a) shows how tulips serving as familiar nursery rhyme might be employed for display on a package. (b) (shows an example in which) tulips are made to partially overlap, being such that from frontmost to backmost they have different colors (the frontmost being red, the one behind that being white, and the backmost being yellow). (c) shows an example in which numbers indicating order of use are further simultaneously displayed.
Figure 1:
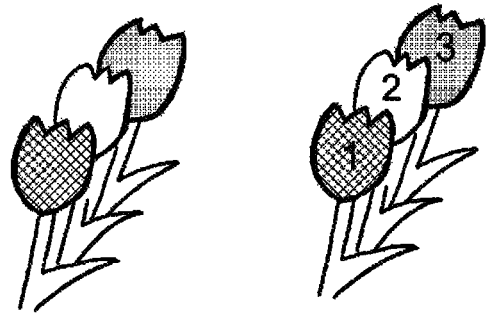

As shown in FIG. 1, a package was manufactured at which displayed on the surface thereof were illustrations that were images of tulips, the frontmost flower being colored red, the flower behind and overlapped by that one being colored white, and the backmost flower further overlapped by that one being colored yellow.

Furthermore, as shown in FIG. 2, an infusion set was manufactured which had three three-way stopcocks having infusion tubing at secondary tubing branches, and which employed shutoff clamps with which the secondary tubing branches were equipped that, starting from the bottom, were respectively colored in order so as to be red, white, and yellow.

In addition, the manufactured infusion set was sterilized and sealed within a package at which displayed on the surface thereof were illustrations that were the aforesaid images of tulips, the frontmost flower being colored red, the flower behind and overlapped by that one being colored white, and the backmost flower further overlapped by that one being colored yellow.

At the foregoing manufactured infusion set, because some of the members making up the sets of secondary tubing were colored, it was possible with just a glance to recognize each set of secondary tubing and the spike at the far end thereof.

Moreover, at the aforesaid package in which the infusion set was sealed, the illustrations depicted on the surface of the package immediately caught the eye, and it was possible to effortlessly recognize that red, white, and yellow coloring was employed in order from the frontmost depicted image to the images that were depicted therebehind. In addition, when the package was opened, it was possible with just a glance to recognize that some of the members making up the sets of secondary tubing in the infusion set that was sealed therewithin were colored with the same colors.

In this way, as a result of making it possible for the order of use of respective sets of infusions in the infusion set to be linked to colors and definitively recognized, it was extremely easy to grasp the administration procedure during use of the infusion set. Furthermore, when numbers indicating order of administration were further displayed in combined fashion with the illustrations displayed on the package, as compared with the situation in which only colors were displayed, it was even easier to grasp the administration procedure during use of the infusion set.

INDUSTRIAL UTILITY

In accordance with the means of the present invention, it is possible to provide a novel infusion set that makes it possible to prevent occurrence of situations in which confusion as to order of use of a plurality of spikes provided at an infusion set when installing infusion container(s) causes error in the order in which infusions are to be administered, or in which infusion(s) containing different drug(s) become mixed up among multiple pieces of infusion tubing when there has been a change in set(s) of infusion(s) at the infusion set, and other accidents such as may occur due to human error, and that moreover makes it possible to easily establish standard procedures for use.

EXPLANATION OF REFERENCE NUMERALS

1 Package
1a Illustration
2 Spike
3 Shutoff clamp
4 Infusion tubing
5 Three-way stopcock
5d Lever
6 Spike cap (with hydrophobic filter and lid)
6b Hydrophobic filter
6d Lid
7 Cap for connector for connection with intravenous drip needle
7b Hydrophobic filter
7d Lid
8 Male connector
9 Drip chamber
10 Roller clamp
11 Filter bag

The invention claimed is:

1. An infusion package comprising:
an infusion set comprising a plurality of infusion groups, each group comprising:
(a) a spike cap;
(b) a spike on which said spike cap is installed;
(c) infusion tubing, one end of which is connected to said spike;
(d) a shutoff clamp for pressing on said infusion tubing and at least one of opening and closing a flow path within said infusion tubing; and
(e) at least one of a stopcock and a splitter which is connected to the other end of said infusion tubing, each of the plurality of infusion groups being given different colors, each of the colors being assigned regarding which of the spikes is to be used during intravenous drip infusion, one or more of the constituent elements of each group being colored with the color assigned for that group, the colors being identical to the colors employed at the images displayed on the package,
a package bag for sealing the infusion set therein, the package bag comprising a plurality of illustrations indicating an order of the infusion groups with respective different colors displayed in mutually offset and partially overlapping fashion on a surface of the package bag.

2. The infusion package according to claim 1, wherein numbers indicating order of administration are further displayed at the illustrations.

* * * * *